US012773107B2

(12) United States Patent
Lang

(10) Patent No.: US 12,773,107 B2
(45) Date of Patent: Oct. 27, 2026

(54) MIRROR ASSEMBLY FOR DENTAL APPLICATIONS

(71) Applicant: EMPERIADENT INC., Dieppe (CA)

(72) Inventor: Justin Lang, Dieppe (CA)

( * ) Notice: Subject to any disclaimer, the term of this patent is extended or adjusted under 35 U.S.C. 154(b) by 0 days.

(21) Appl. No.: 18/745,651

(22) Filed: Jun. 17, 2024

(65) Prior Publication Data

US 2024/0415380 A1 Dec. 19, 2024

Related U.S. Application Data

(60) Provisional application No. 63/521,386, filed on Jun. 16, 2023.

(51) Int. Cl.
*A61B 1/247* (2006.01)

(52) U.S. Cl.
CPC .................................... *A61B 1/247* (2013.01)

(58) Field of Classification Search
CPC ...................................................... A61B 1/247
See application file for complete search history.

(56) References Cited

U.S. PATENT DOCUMENTS 673,019 A * 4/1901 Gilbert ................. G09B 23/283 211/13.1
1,584,323 A * 5/1926 Price et al. ............. A47F 11/04 434/371
3,599,334 A * 8/1971 Warden .................. A61B 1/247 433/31
2004/0023184 A1* 2/2004 de Josselin de Jong .................... A61B 1/0676 433/30
2004/0137405 A1* 7/2004 Fang .................... A61C 13/245 433/167
2005/0202362 A1* 9/2005 Ostler ...................... A61K 8/22 433/31
2006/0105288 A1* 5/2006 Garfinkel ............... A61B 1/247 433/76
2010/0129767 A1* 5/2010 Fishburne, Jr. ........ A61B 1/247 433/136
2018/0153641 A1* 6/2018 Harlan ..................... A61C 3/00

FOREIGN PATENT DOCUMENTS

DE 102005017861 A1 * 2/2007 ........... A61B 1/0676

OTHER PUBLICATIONS

"Adjacent." Merriam-Webster.com Dictionary, Merriam-Webster, https://www.merriam-webster.com/dictionary/adjacent. Accessed Nov. 6, 2025. (Year: 2025).*

* cited by examiner

*Primary Examiner* — Heidi M Eide
(74) *Attorney, Agent, or Firm* — Alessandro Colonnier; Andrews Robichaud

(57) ABSTRACT

The present disclosure provides a mirror assembly for dental applications. There is a need for a device that helps communication between patients and their dentists. The present mirror assembly provides a reference point to enhance communication. The mirror assembly comprises a mirror glass having a reflective surface, a frame surrounding the mirror glass, and one or more molded teeth positioned on the frame. The one or more molded teeth may be reflected by the mirror glass, and the mirror assembly may be viewed by the patient, the dentist, or both.

14 Claims, 4 Drawing Sheets

MIRROR ASSEMBLY FOR DENTAL APPLICATIONS

CROSS REFERENCE TO RELATED APPLICATION

The present document claims priority to U.S. Provisional Patent Application No. 63/521,386, entitled "Dentist/Patient Arch-View Mirror" filed on Jun. 16, 2023, the contents of which are incorporated herein by reference in their entirety.

FIELD OF THE INVENTION

This invention pertains to an instrument used by a dentist to describe a dental work plan to a patient. More particularly, it pertains to a model teeth arrangement molded around a hand-held mirror.

BACKGROUND

Traditionally, a visit to a conventional dentist is rarely a pleasant and enjoyable experience. Young children especially anticipate these visits with anxiety. Therefore, it is believed that there is a need in the field of dentistry to reduce the mystery and fear of pain surrounding dental work. There is a need in this field for a device or a method to help a dentist to open a dialogue with a patient.

SUMMARY

In the present disclosure, the terms "telltale mirror", "telltale arch-view mirror", and "mirror assembly" are used interchangeably to refer to the same element.

In an aspect, the present disclosure provides a mirror assembly for use in dental applications, the mirror assembly comprising: a mirror glass providing a reflective surface; a frame surrounding the mirror glass, thereby framing the mirror glass; and, one or more molded teeth positioned on the frame, whereby the one or more molded teeth may be used as a reference.

In the present invention, there is provided a hand-held mirror embodying an open mouth with a full set of teeth molded along the edge of the mirror. The mirror gives a full arch view of a patient's mouth and teeth arrangement. By tilting the mirror, the user can see the inside surfaces of the molded teeth as a reflection in the mirror. A dentist can point at the molded teeth and explain a procedure to be done to the patient's teeth arrangement. The hand-held mirror has the appearance of an arcade toy, with a pleasant and friendly shape, appealing to children and young adults.

In another aspect of the hand-held mirror, referred to herein after as the telltale mirror, is that the mirror has a magnification of about 10× and has an LED light source in the frame thereof, causing the frame to glow. It is believed that the telltale mirror, with its overall arcade toy-like appearance facilitates access by a young patient into a dentist's chair.

The user of the hand-held mirror becomes absorbed by the view of the inside of his/her own mouth and does not see the dentist coming with a syringe or a pair of forceps. Therefore, it is also believed that the telltale mirror gives a patient a sense of self control, and a more relaxed disposition.

BRIEF DESCRIPTION OF THE DRAWINGS

The following figures serve to illustrate various embodiments of features of the disclosure. These figures are illustrative and are not intended to be limiting.

DETAILED DESCRIPTION

The following embodiments are merely illustrative and are not intended to be limiting. It will be appreciated that various modifications and/or alterations to the embodiments described herein may be made without departing from the disclosure and any modifications and/or alterations are within the scope of the contemplated disclosure.

The telltale mirror according to the preferred embodiment of the present invention is described herein below in terms of its structure, operation, and function.

According to an embodiment of the present disclosure, a mirror assembly for use in dental applications is provided, the mirror assembly comprising: a mirror glass providing a reflective surface; a frame surrounding the mirror glass, thereby framing the mirror glass; and, one or more molded teeth positioned on the frame, whereby the one or more molded teeth may be used as a reference.

In another embodiment of the present disclosure, the mirror glass reflects one or more teeth of a patient, thereby allowing the patient to compare a reflected one or more teeth of the patient with the one or more molded teeth.

In another embodiment of the present disclosure, the mirror glass allows the patient to compare the reflected one or more teeth of the patient with a reflection of the one or more molded teeth.

In another embodiment of the present disclosure, the one or more molded teeth extend away from the mirror glass.

In another embodiment of the present disclosure, the one or more molded teeth are positioned adjacent to an outer edge of the mirror glass.

In another embodiment of the present disclosure, the one or more molded teeth each comprise an inner surface that may be reflected by the mirror glass for viewing by a patient.

In another embodiment of the present disclosure, the mirror glass has magnification, thereby allowing the mirror glass to magnify at least one of one or more teeth of a patient and the one or more molded teeth.

In another embodiment of the present disclosure, the one or more molded teeth comprise at least one arch of molded teeth.

In another embodiment of the present disclosure, the one or more molded teeth comprise a full set of molded teeth.

In another embodiment of the present disclosure, the frame comprises a light source to illuminate the mirror glass.

In another embodiment of the present disclosure, the mirror assembly further comprises at least one handle extending from the frame.

In another embodiment of the present disclosure, the at least one handle comprises at least one push button to activate the light source.

Figures 1, 2:
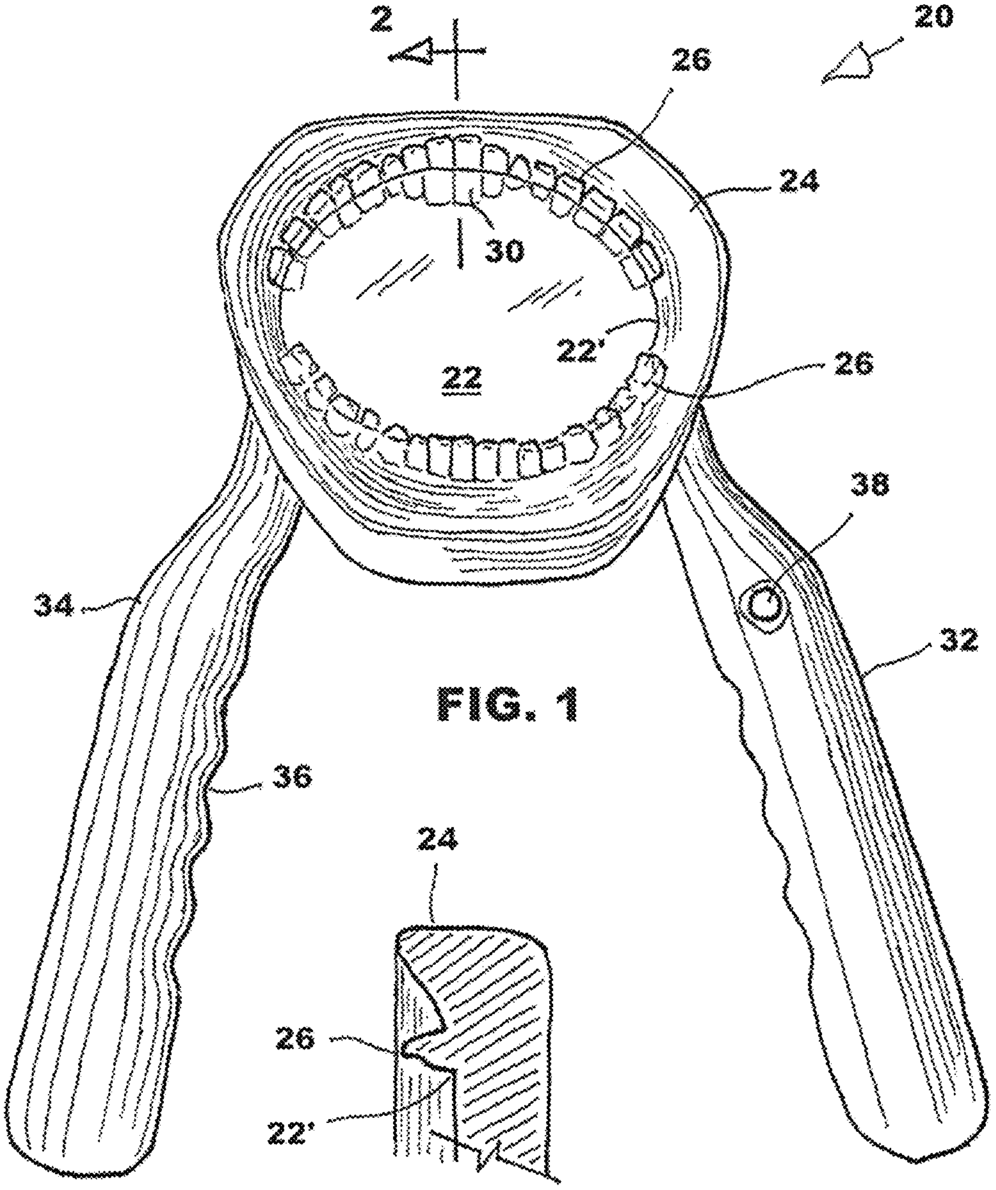
FIG. 1 is a first plane view of the telltale mirror.
FIG. 2 is a cross-section view across the frame of the telltale mirror along line 2 in FIG. 1.

Referring to FIG. 1, the preferred telltale mirror 20 is comprised of a mirror glass 22 surrounded by a frame 24 on which is molded a set of normal-size teeth 26. The hand-held mirror 20 embodies a wide-open mouth with a full set of teeth. The molded teeth form a frame around the mirror. The telltale mirror 20 has the shape of an open mouth, for association with dentistry. The molded teeth 26 extend away from the mirror glass 22 along the edge 22' of the mirror. By tilting the preferred telltale mirror 20 the user can see a reflection of the inside surfaces 30 of the front teeth for example as illustrated in FIG. 1. The inside surfaces of a patient's teeth are not visible to the patient by looking in a conventional mirror. Using this telltale mirror 20 a patient can easily associate the molded teeth with his/her own teeth and imagine what the dentist saw on the hidden surfaces of his/her own teeth. It will be appreciated that although only the inside surfaces of the front teeth is visible in FIG. 1, the mirror can be tilted other ways to see the inside surfaces of all other molded teeth.

Figure 7:
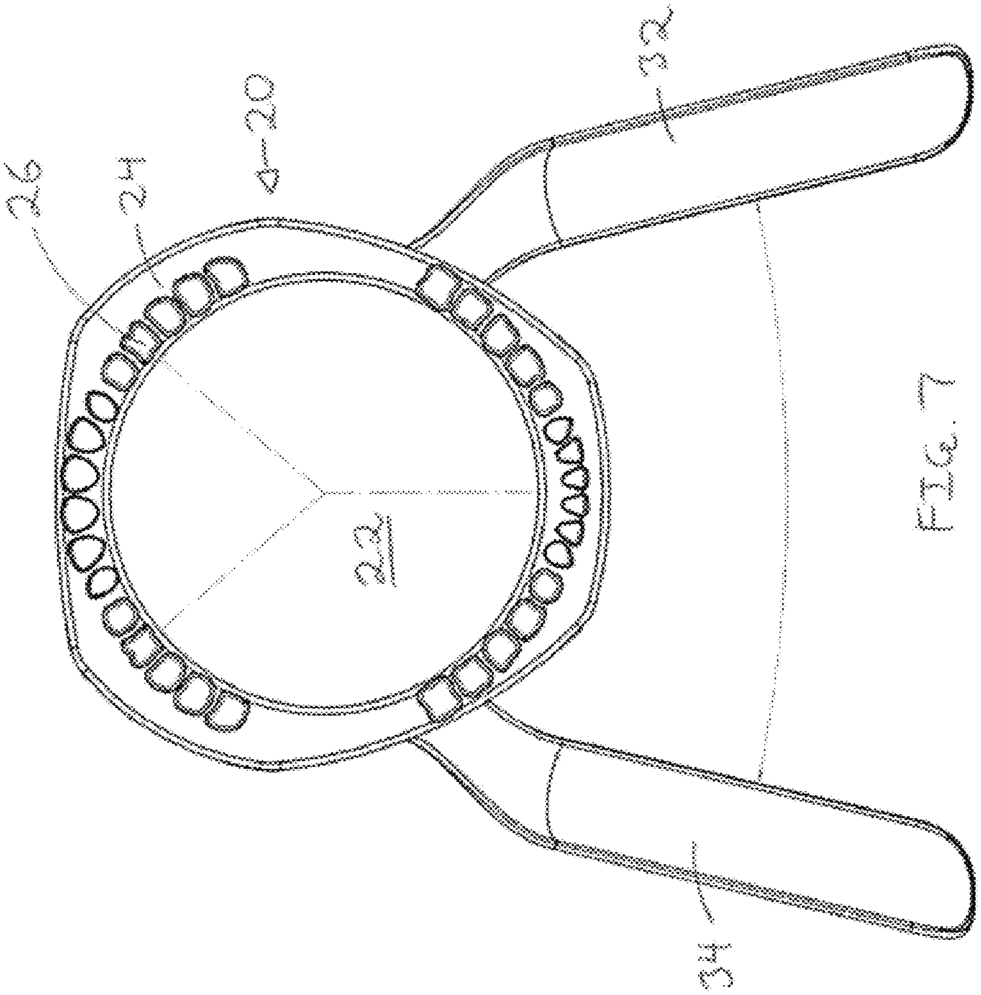
FIG. 7 is a second plane view of the telltale mirror.
Figure 6:
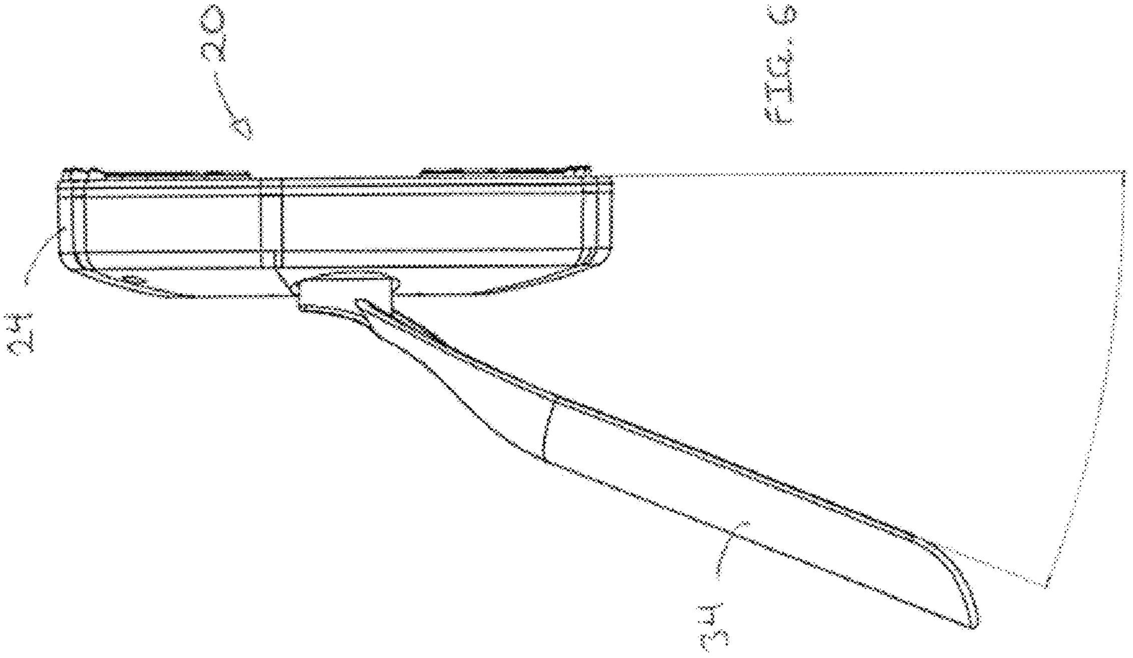
FIG. 6 is a second side view of the telltale mirror.

The preferred telltale mirror 20 has two handles 32, 34 with finger grips 36. These handles 32, 34 are spaced-apart and angled to simulate a video game emulator console, or the console of other arcade machines. According to an embodiment of the present disclosure, and as best shown in FIG. 6, an angle between the frame 24 and the handles 32, 34 is within the range of 15° to 45°. In a preferred embodiment, the angle between the frame 24 and the handles 32, 34 is 22°. According to another embodiment of the present disclosure, and as best shown in FIG. 7, an angle between the handles 32 and 34 is within the range of 10° to 80°. In a preferred embodiment, the angle between the handles 32 and 34 is 25°. One of the handles 32, 34 has a push button 38 thereon to activate a LED light source (not shown) in the frame 24 of the telltale mirror 20.

The preferred mirror glass 22 has a magnification of 10X for example. Such magnification makes it more interesting for a patient to follow the dentist's work, and to focus on magnified details inside his/her own mouth as opposed to concentrate on the fear of the unknown. The frame 24 of the preferred mirror is made of translucent material and the light source inside the frame 24 causes the frame 24 glow thereby providing indirect lighting toward the mirror 22, and the glowing appearance of an arcade machine.

Referring now to FIG. 2, the molded teeth 26 are positioned along the edge 22' of the mirror glass 22. The molded teeth 26 project away from the mirror glass 22 as illustrated. The frame 24 has a shape simulating the gums and lips combination with a thickness that is as much as the protrusion of the teeth 26, from the mirror glass 22, as can be seen in FIG. 2. When the preferred telltale mirror 20 is placed face down on a table for example, the frame 24 sits firmly on the surface of the table. The telltale mirror 20 is also easy to clean and to disinfect between uses.

Figure 3:
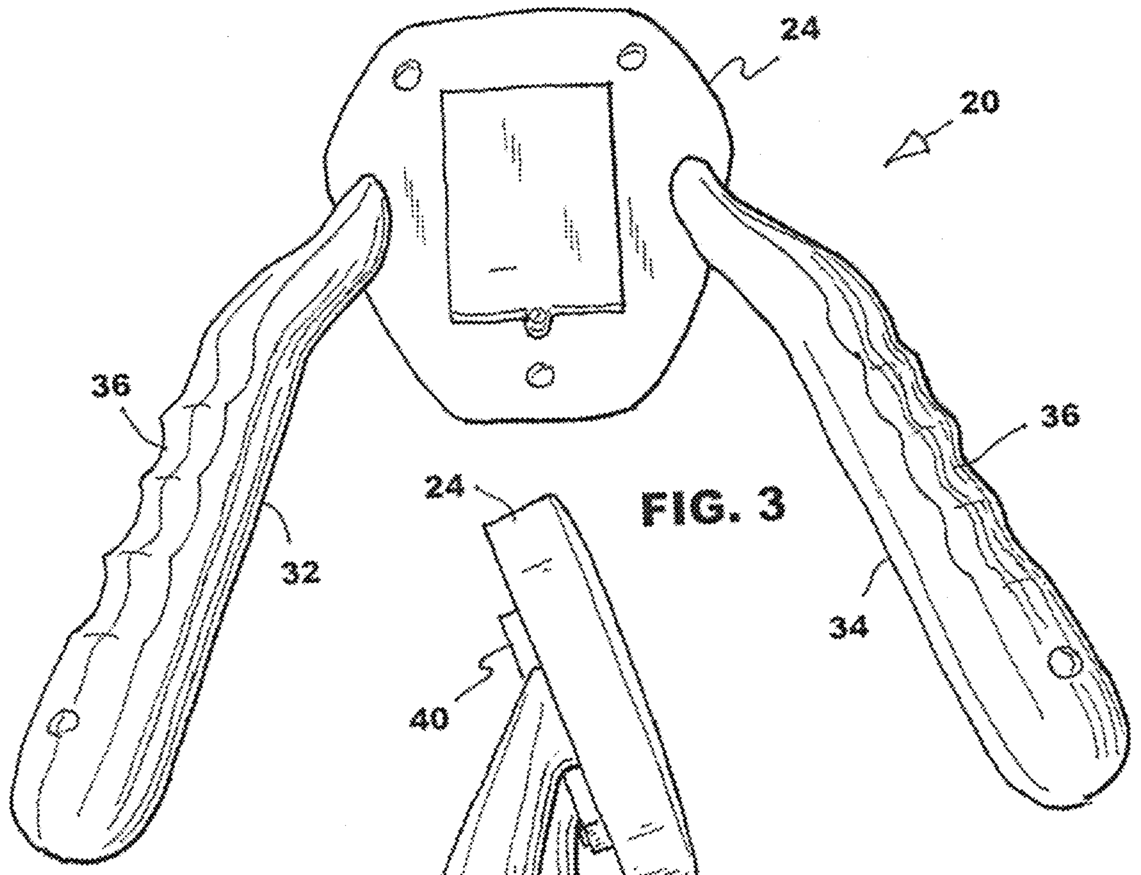
FIG. 3 is a rear view of the telltale mirror.
Figure 4:
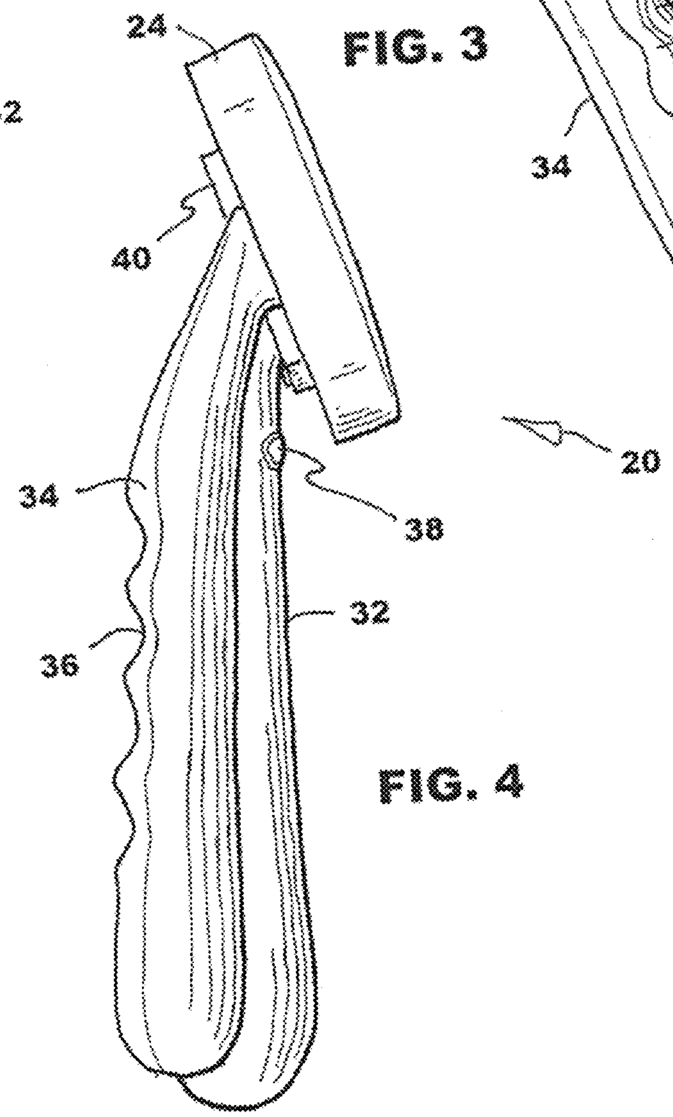
FIG. 4 is a first side view of the telltale mirror.

Referring now to FIGS. 3 and 4, the preferred telltale mirror 20 is made of plastic for example and has an openable door 40 on the back of the frame 24 giving access to circuitry, LED lights and a battery compartment (not shown) behind the mirror glass 22.

Although only one push button 38 is illustrated and described in the drawings, some embodiments might have one push button on each handle, each causing the frame to glow one specific color, or a third color when both push buttons are depressed at the same time.

Figure 5:
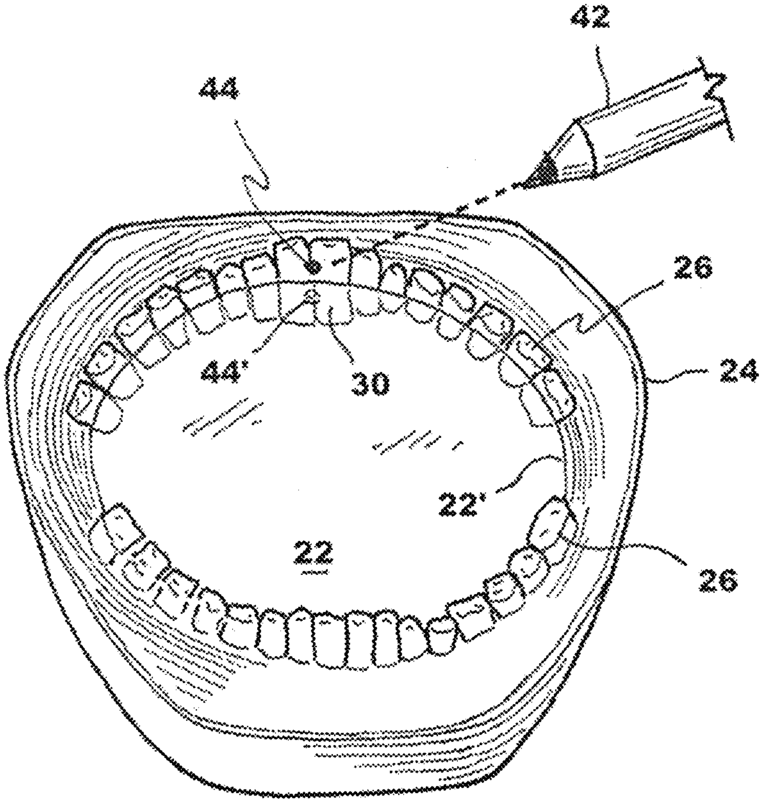
FIG. 5 is an enlarged plan view of the telltale mirror and mirror frame.

Referring now to FIG. 5, the preferred method of use of the preferred telltale mirror 20 will be described. Following a first examination of a patient's teeth using a common dental mirror, a dentist can use a washable-ink marker 42 to draw a cavity 44, for example, on the molded teeth of the mirror, at a same location as found on the patient's teeth. The patient can now relate to the location of the cavity in his/her own teeth, by looking at the model image in the mirror. When the cavity is drawn on the inside surface of the front teeth as illustrated, the patient can still see it directly at label 44, or as a reflection 44' in the mirror. Such reflection view 44' is unavailable when looking at a common mirror. The present mirror assembly 20 can therefore act as a communication tool by providing a reference point for the patient, the dentist, or simultaneously for both the patient and the dentist.

While a patient has his/her mind focusing on the mirror and the arch view of his/her own mouth, the dentist can have a conversation with a patient to explain a work plan. The same pen and drawing procedure can be used to illustrate plaque cleaning, root canals, tooth capping for examples, and good dental hygiene. It is believed that the toy-like appearance of the telltale arch-view mirror 20 facilitates a conversation between a dentist and a patient by guiding the patient's attention away from a traditional fear-of-pain emotional disposition.

Many modifications of the embodiments described herein as well as other embodiments may be evident to a person skilled in the art having the benefit of the teachings presented in the foregoing description and associated drawings. It is understood that these modifications and additional embodiments are captured within the scope of the contemplated disclosure which is not to be limited to the specific embodiment disclosed.

The invention claimed is:

1. A mirror assembly for use in dental applications, the mirror assembly comprising:
- a mirror glass providing a reflective surface;
- a frame surrounding the mirror glass, thereby framing the mirror glass;
- one or more molded teeth positioned on the frame, whereby the one or more molded teeth may be used as a reference; and,
- two handles extending from the frame, wherein the handles are spaced apart to form a first angle and a second angle, wherein the second angle is within a range of 10° to 80°.

2. The mirror assembly of claim 1, wherein the mirror glass is configured to reflect one or more teeth of a patient, thereby allowing the patient to compare a reflected one or more teeth of the patient with the one or more molded teeth.

3. The mirror assembly of claim 2, wherein the mirror glass allows the patient to compare the reflected one or more teeth of the patient with a reflection of the one or more molded teeth.

4. The mirror assembly of claim 1, wherein the one or more molded teeth extend away from the mirror glass.

5. The mirror assembly of claim 1, wherein the one or more molded teeth are positioned adjacent to an outer edge of the mirror glass.

6. The mirror assembly of claim 5, wherein the one or more molded teeth each comprise an inner surface that may be reflected by the mirror glass for viewing by a patient.

7. The mirror assembly of claim 1, wherein the mirror glass has magnification, thereby allowing the mirror glass to magnify at least one of one or more teeth of a patient and the one or more molded teeth.

8. The mirror assembly of claim 1, wherein the one or more molded teeth comprise at least one arch of molded teeth.

9. The mirror assembly of claim 1, wherein the one or more molded teeth comprise a full set of molded teeth.

10. The mirror assembly of claim 1, wherein the frame comprises a light source to illuminate the mirror glass.

11. The mirror assembly of claim 10, wherein one handle of the at least two handles comprises at least one push button to activate the light source.

12. The mirror assembly of claim 1, wherein the first angle is within the range of 15° to 45°.

13. The mirror assembly of claim 12, wherein the first angle is 22°.

14. The mirror assembly of claim 1, wherein the second angle is 25°.

* * * * *